(12) United States Patent
Kashef et al.

(10) Patent No.: US 9,642,536 B2
(45) Date of Patent: May 9, 2017

(54) MENTAL STATE ANALYSIS USING HEART RATE COLLECTION BASED ON VIDEO IMAGERY

(71) Applicant: Affectiva, Inc., Boston, MA (US)

(72) Inventors: Youssef Kashef, Obour (EG); Rana el Kaliouby, Boston, MA (US); Ahmed Adel Osman, New Cairo (EG); Niels Haering, Reston, VA (US); Viprali Bhatkar, Cambridge, MA (US)

(73) Assignee: Affectiva, Inc., Boston, MA (US)

( * ) Notice: Subject to any disclaimer, the term of this patent is extended or adjusted under 35 U.S.C. 154(b) by 0 days.

(21) Appl. No.: 14/214,719

(22) Filed: Mar. 15, 2014

(65) Prior Publication Data

US 2014/0200416 A1     Jul. 17, 2014

Related U.S. Application Data

(63) Continuation-in-part of application No. 13/153,745, filed on Jun. 6, 2011.
(Continued)

(51) Int. Cl.
*A61B 5/00*      (2006.01)
*A61B 5/0205*   (2006.01)
(Continued)

(52) U.S. Cl.
CPC ........ *A61B 5/02055* (2013.01); *A61B 5/0077* (2013.01); *A61B 5/165* (2013.01);
(Continued)

(58) Field of Classification Search
None
See application file for complete search history.

(56) References Cited

U.S. PATENT DOCUMENTS 3,034,500 A     5/1962   Backster, Jr.
3,548,806 A    12/1970   Fisher
(Continued)

FOREIGN PATENT DOCUMENTS

JP            08115367           7/1996
KR   10-2005-0021759 A          3/2005
(Continued)

OTHER PUBLICATIONS

Wu, Hao-Yu, "Eulerian video magnifcation for revealing subtle changes in the world", Journal ACM Transactions on Graphics (TOG), vol. 31 Issue 4, Jul. 2012 Article No. 65.*
(Continued)

*Primary Examiner* — Chan Park
*Assistant Examiner* — Elisa Rice
(74) *Attorney, Agent, or Firm* — Adams Intellex, PLC

(57) ABSTRACT

Video of one or more people is obtained and analyzed. Heart rate information is determined from the video and the heart rate information is used in mental state analysis. The heart rate information and resulting mental state analysis are correlated to stimuli, such as digital media which is consumed or with which a person interacts. The heart rate information is used to infer mental states. The mental state analysis, based on the heart rate information, can be used to optimize digital media or modify a digital game.

32 Claims, 5 Drawing Sheets

Related U.S. Application Data

(60) Provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011, provisional application No. 61/793,761, filed on Mar. 15, 2013, provisional application No. 61/789,038, filed on Mar. 15, 2013, provisional application No. 61/790,461, filed on Mar. 15, 2013, provisional application No. 61/798,731, filed on Mar. 15, 2013, provisional application No. 61/844,478, filed on Jul. 10, 2013, provisional application No. 61/916,190, filed on Dec. 14, 2013, provisional application No. 61/924,252, filed on Jan. 7, 2014, provisional application No. 61/927,481, filed on Jan. 15, 2014.

(51) Int. Cl.
| | | |
|---|---|---|
| A61B 5/16 | (2006.01) | |
| G06F 19/00 | (2011.01) | |
| A61B 5/024 | (2006.01) | |
| G06Q 30/02 | (2012.01) | |
| A61B 5/11 | (2006.01) | |

(52) U.S. Cl.
CPC ...... G06F 19/3418 (2013.01); G06F 19/3481 (2013.01); *A61B 5/02405* (2013.01); *A61B 5/1114* (2013.01); *A61B 5/441* (2013.01); *G06F 19/345* (2013.01); *G06Q 30/0242* (2013.01); *G06Q 30/0271* (2013.01)

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstrom et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,358,201 B1 | 3/2002 | Childre et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,013,478 B1 | 3/2006 | Hendricks et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,239,000 B1 * | 8/2012 | Morris et al. ............ 600/410 |
| 8,401,248 B1 | 3/2013 | Moon et al. |
| 8,442,638 B2 | 5/2013 | Libbus et al. |
| 8,522,779 B2 | 9/2013 | Lee et al. |
| 8,529,447 B2 | 9/2013 | Jain et al. |
| 8,540,629 B2 | 9/2013 | Jain et al. |
| 8,600,120 B2 | 12/2013 | Gonion et al. |
| 8,977,347 B2 | 3/2015 | Mestha et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |

(56) References Cited

U.S. PATENT DOCUMENTS

| | | |
|---|---|---|
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0078513 A1 | 4/2003 | Marshall |
| 2003/0093784 A1 | 5/2003 | Dimitrova et al. |
| 2003/0191682 A1 | 10/2003 | Shepard et al. |
| 2003/0191816 A1 | 10/2003 | Landress et al. |
| 2004/0181457 A1 | 9/2004 | Biebesheimer et al. |
| 2004/0236236 A1* | 11/2004 | Yanagidaira ............ A61B 5/18 600/509 |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0115157 A1 | 6/2006 | Mori |
| 2006/0143647 A1 | 6/2006 | Bill |
| 2006/0235753 A1 | 10/2006 | Kameyama |
| 2007/0167689 A1 | 7/2007 | Ramadas et al. |
| 2007/0239787 A1 | 10/2007 | Cunningham et al. |
| 2007/0255831 A1 | 11/2007 | Hayashi et al. |
| 2007/0299964 A1 | 12/2007 | Wong et al. |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2009/0006206 A1 | 1/2009 | Groe et al. |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0210290 A1 | 8/2009 | Elliott et al. |
| 2009/0217315 A1 | 8/2009 | Malik et al. |
| 2009/0270170 A1* | 10/2009 | Patton ............................ 463/36 |
| 2009/0271417 A1 | 10/2009 | Toebes et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0266213 A1 | 10/2010 | Hill |
| 2010/0274847 A1 | 10/2010 | Anderson et al. |
| 2010/0324437 A1* | 12/2010 | Freeman et al. ............. 600/529 |
| 2011/0092780 A1 | 4/2011 | Zhang et al. |
| 2011/0126226 A1 | 5/2011 | Makhlouf |
| 2011/0143728 A1 | 6/2011 | Holopainen et al. |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0260830 A1* | 10/2011 | Weising .................. G06F 3/015 340/5.52 |
| 2011/0263946 A1 | 10/2011 | el Kaliouby et al. |
| 2012/0293548 A1 | 11/2012 | Perez et al. |
| 2012/0302904 A1 | 11/2012 | Lian et al. |
| 2012/0304206 A1 | 11/2012 | Roberts et al. |
| 2013/0006124 A1 | 1/2013 | Eyal et al. |
| 2013/0116587 A1 | 5/2013 | Sornmo et al. |
| 2013/0197409 A1 | 8/2013 | Baxter et al. |

FOREIGN PATENT DOCUMENTS

| | | |
|---|---|---|
| KR | 10-2008-0016303 A | 2/2008 |
| KR | 1020100048688 A | 5/2010 |
| KR | 100964325 B1 | 6/2010 |
| KR | 1020100094897 A | 8/2010 |
| WO | WO 2011/045422 A1 | 4/2011 |

OTHER PUBLICATIONS

Rana Ayman El Kaliouby, Mind-reading machines: automated inference of complex mental states, Jul. 2005, University of Cambridge, Cambridge, United Kingdom.

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

* cited by examiner

MENTAL STATE ANALYSIS USING HEART RATE COLLECTION BASED ON VIDEO IMAGERY

RELATED APPLICATIONS

This application claims the benefit of U.S. provisional patent applications "Mental State Analysis Using Heart Rate Collection Based on Video Imagery" Ser. No. 61/793,761, filed Mar. 15, 2013, "Mental State Analysis Using Blink Rate" Ser. No. 61/789,038, filed Mar. 15, 2013, "Mental State Data Tagging for Data Collected from Multiple Sources" Ser. No. 61/790,461, filed Mar. 15, 2013, "Mental State Well Being Monitoring" Ser. No. 61/798,731, filed Mar. 15, 2013, "Personal Emotional Profile Generation" Ser. No. 61/844,478, filed Jul. 10, 2013, "Heart Rate Variability Evaluation for Mental State Analysis" Ser. No. 61/916,190, filed Dec. 14, 2013, "Mental State Analysis Using an Application Programming Interface" Ser. No. 61/924,252, filed Jan. 7, 2014, and "Mental State Analysis for Norm Generation" Ser. No. 61/927,481, filed Jan. 15, 2014. This application is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The foregoing applications are each hereby incorporated by reference in their entirety.

FIELD OF ART

This application relates generally to analysis of mental states, and more particularly to mental state analysis using heart rate collection based on video imagery.

BACKGROUND

It is well known that an individual's emotions or mental state can cause physiological changes. Examples of such physiological changes include sweating, changes in respiration, facial movements, fidgeting, changes to blood pressure, and changes to heart rate. Heart-rate related indications of mental state can include a measure of absolute heart rate (HR), heart rate variability (HRV), and blood volume pulse (BVP). An individual's heart rate can be measured in various ways, including using a medical electrocardiograph (EKG) machine, a chest strap with electrodes, a pulse oximeter that clips on a finger, a sphygmomanometer, or by measuring a pressure point on an individual.

A person's mental state can be impacted by many types of external stimuli. One growingly common stimulus is interaction with a computer. People spend an ever-increasing amount of time interacting with computers, and consume a vast amount of computer-delivered media. This interaction can be for many different reasons, such as desire for educational content, entertainment, social media interaction, document creation, and gaming, to name a few.

In some cases, the human-computer interaction can take the form of a person performing a task using a computer and a software tool running on the computer. Examples of such interactions can include filling out a tax form, creating a document, editing a video, and doing one or more of the other activities that a modern computer can perform. The person might find certain activities interesting or even exciting, and might be surprised at how easy it is to perform the activity or activities. The person can become excited, happy, or content as they perform the activities. On the other hand, the person might find some activities difficult to perform, and can become frustrated or even angry with the computer, even though the computer is oblivious to their emotions. In other cases of human-computer interaction, the person can be consuming content or media such as news, pictures, music, or video. A person's mental state can be useful in determining whether or not the person enjoys particular media content.

Currently, tedious methods with limited usefulness are employed to determine users' mental states. For example, users can be surveyed in an attempt to determine their mental state in reaction to a stimulus such as a human-computer interaction. Survey results are often unreliable because the surveys are often done well after the activity was performed, survey participation rates can be low, and many times people do not provide accurate and honest answers to the survey questions. In other cases, people can self-rate media to communicate personal preferences by entering a specific number of stars corresponding to a level of like or dislike. However, these types of subjective evaluations are often neither a reliable nor practical way to evaluate personal response to media. Recommendations based on such methods are imprecise, subjective, unreliable, and are often further subject to problems related to the small number of individuals willing to participate in the evaluations.

SUMMARY

Heart rate and other types of analysis can be gleaned from facial video as someone observes various media presentations. The information on heart rates can be used to aid in mental state analysis. A method for mental state analysis is described which includes obtaining video of an individual as the individual is interacting with a computer, either by performing various operations or by consuming a media presentation. The video is then analyzed to determine heart rate information on the individual including both heart rate and heart rate variability. A mental state of the individual is then inferred based on the heart rate information. A computer-implemented method for mental state analysis is disclosed comprising: obtaining video of an individual; analyzing the video to determine heart rate information; and inferring mental states of the individual based on the heart rate information.

The method can include analyzing a media presentation based on the mental states, which were inferred. The analyzing of the media presentation may include evaluating advertisement effectiveness. The analyzing of the media presentation can also include optimizing the media presentation. The heart rate information may be correlated to a stimulus that the individual is encountering. The analyzing can include identifying a location of a face of the individual in a portion of the video. The method may further comprise establishing a region of interest including the face, separating pixels in the region of interest into at least two channel values and combining to form raw traces, transforming and decomposing the raw traces into at least one independent source signal, and processing the at least one independent source signal to obtain the heart rate information.

In embodiments, a computer program product embodied in a non-transitory computer readable medium for mental state analysis comprises: code for obtaining video of an individual; code for analyzing the video to determine heart rate information; and code for inferring mental states of the individual based on the heart rate information. In some embodiments, a computer system for mental state analysis comprises: a memory which stores instructions; one or more processors attached to the memory wherein the one or more processors, when executing the instructions which are stored, are configured to: obtain video of an individual; analyze the video to determine heart rate information; and infer mental states of the individual based on the heart rate information.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
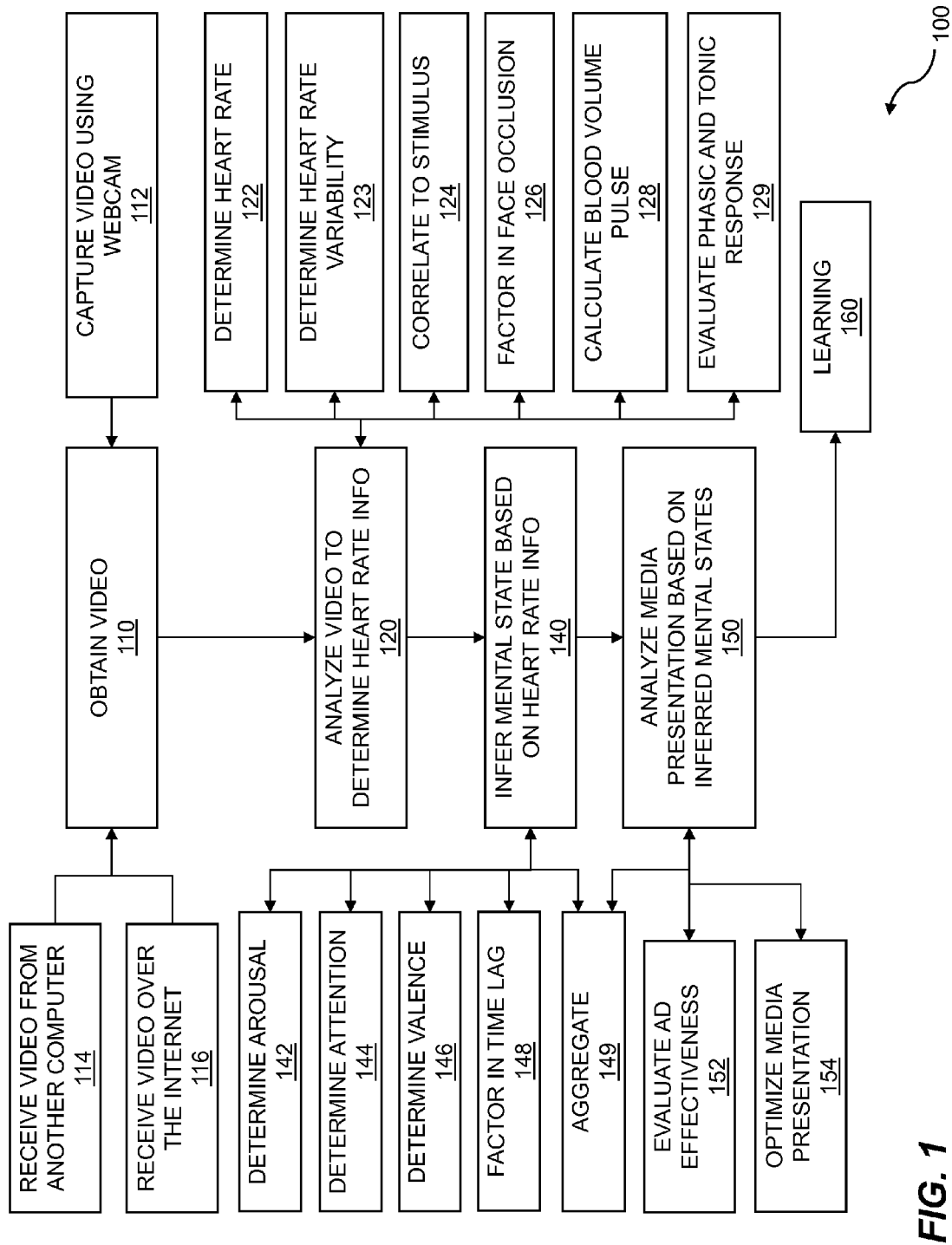
FIG. 1 is a flow diagram for mental state analysis.

As an individual interacts with a computer, the individual's mental state can be impacted by the interaction, which can in turn have an impact on the individual's facial expressions and heart rate, as well as provoking other physiological reactions. Determining the individual's mental state can have value for a variety of reasons, such as improving the program that the individual is using, rating a media presentation, or optimizing an advertisement. Traditional methods of monitoring an individual's mental state have limited effectiveness for a variety of reasons. For example, surveys or rating systems are prone to non-participation and inaccurate reporting, and even though physiological information is often an accurate way to determine an individual's mental state, traditional physiological monitoring devices are intrusive and not available at most computer workstations.

Many contemporary computer systems already include a webcam, and even for systems without a webcam, it is possible to easily and inexpensively add one to nearly any modern computer workstation. In many cases, a webcam can unobtrusively monitor an individual, but until recently it was not known how to determine heart rate information from a video produced by a webcam. Recent studies have shown, however, that it is possible to extract heart rate information from video of an individual. Examples of such work include "Remote plethysmographic imaging using ambient light" by Wim Verkruysse, Lars O Svaasand, and J Stuart Nelson, published in Optics Express, Vol. 16, No. 26, on Dec. 12, 2008, and U.S. patent application publication US 2011/0251493 A1, published on Oct. 31, 2011, entitled "Method and System for Measurement of Physiological Parameters;" with Ming-Zher Poh, Daniel McDuff, and Rosalind Picard as named inventors. These papers are hereby incorporated by reference in their entirety. The present disclosure describes using a video of an individual to determine heart rate information and then using the heart rate information to infer a mental state of that individual.

An individual can interact with a computer to perform some type of task on the computer, or view a media presentation while being monitored by a webcam. The video from the webcam can then be analyzed to determine heart rate information. In one embodiment, the video is separated into separate color channels and a trace is generated for each color channel based on the spatial average of the color channel for the face over time. Independent component analysis can then be used to generate independent source signals that correlate to heart rate information, such as BVP. Standard signal processing techniques can then be used to extract heart rate information, including heart rate variability, arrhythmias, heart murmurs, beat strength and shape, artery health, or arterial obstructions. In some embodiments, respiration rate information is also determined.

Once the heart rate information has been determined, a mental state of the individual can be inferred. Mental states which can be inferred include confusion, disappointment, hesitation, cognitive overload, focusing, engagement, attention, boredom, exploration, confidence, trust, delight, disgust, skepticism, doubt, satisfaction, excitement, laughter, calmness, happiness, sadness, anger, stress, sentimentality, or curiosity. Various types of heart rate information can be used to infer a mental state. For example, an elevated HR can indicate excitement, a decrease in phasic HR can indicate attention, and tonic HR can be used to indicate arousal. In some embodiments, the heart rate information can be used in conjunction with facial movement data and/or other biosensor data to infer a mental state.

FIG. 1 is a flow diagram 100 for mental state analysis. The flow 100 describes a computer-implemented method for mental state analysis. The flow 100 includes obtaining video 110 of an individual. In some embodiments the video is captured using a webcam 112 while in other embodiments the video is received from another computer 114 and/or over the Internet 116. The video can be color video and can be of various spatial resolutions, frame rates (temporal resolution), and lengths. In some embodiments, a video clip of at least one to three seconds of video is obtained, but in other embodiments, a video clip of 20 seconds or more is obtained. In some embodiments video is continuously captured, while in other embodiments, video is broken into segments, such as 20 second segments, for analysis. Some embodiments continuously analyze the video. In some embodiments the video is a standard resolution television-type video at resolutions such as 720×540, 720×480 or 640×480 pixels with a frame rate of 25 or 30 frames per second (FPS) interlaced or progressive. In other embodiments, the video is a high-definition video at resolutions such as 1280×720 pixels progressive or 1920×1080 interlaced with a frame rate of 30 to about 60 FPS. But, in some embodiments, the video can be at a lower spatial and/or temporal resolution as can commonly be captured by an inexpensive webcam, such as CIF (352×240), QCIF (176× 120) or another video type at a lower resolution and with a frame rate of 25 FPS or lower, about 15 FPS for example. In some embodiments, the video can include a series of images of the individual, and the video can have a variable frame rate. In some embodiments, a specialty camera capable of capturing high frame rate video, such as video with a frame rate faster than 60 FPS, can be used. Some embodiments include video processed at 0.1 (FPS) and above, frame sizes of 1 pixel and above, and even image sequences at irregular temporal sampling and spatial sizes. In embodiments, the method includes converting the video to a constant frame rate and performing filtering on the video to facilitate the analyzing.

The flow 100 continues by analyzing the video to determine heart rate information 120. The analyzing can be performed using any type of algorithm, but one algorithm that can be used is described in more detail in FIG. 3. In some embodiments, the heart rate information includes a measure of heart rate (HR) 122. The heart rate can be an instantaneous heart rate or an average heart rate over a period of time. In some embodiments, the heart rate information includes heart rate variability (HRV) 123. In some embodiments, the analyzing correlates the heart rate information to a stimulus 124 such as a scene of a movie, a portion of an advertisement, a specific task performed within a software application, or any other type of stimulus generated by the individual's interaction with the computer, by an external event, or through some other context. The context can include viewing a concept, viewing a product, and interacting with a person or persons. In some cases a wearable apparatus can view and record another person's face. The video from that person's face can then be analyzed for heart rate information. In some embodiments, two or more people can each have a wearable apparatus and video information can be collected, analyzed, and exchanged between the people or provided to another system for utilization. The analyzing can factor in a facial occlusion 126 for part of an individual's face. This is accomplished in some embodiments by recognizing that the face is occluded and adjusting a region of interest for the frames where the face is partially occluded, along with removing the frames where more than a predetermined portion of the face is occluded. In some embodiments, the analyzing includes calculating blood volume pulse (BVP) 128. The BVP can be included in the heart rate information, and/or can be used to calculate the heart rate information, depending on the embodiment.

The analyzing can include evaluating phasic and/or tonic response 129 of the heart rate information. A phasic response is a short term, or high frequency, response to a stimulus, and a tonic response is a long term, or low frequency, response to a stimulus. In one embodiment, a phasic response constitutes a heartbeat-to-heartbeat difference, while in other embodiments a phasic response constitutes a difference over some number of seconds, such as a period between about two and about 10 seconds. Other embodiments can use a different threshold for a phasic response. A tonic response can represent a change over a longer period of time, for example a change observed during any period of time from 10 seconds to many minutes or longer. HR, HRV and BVP can all have both phasic and tonic responses. In addition, analyzing can include extracting a heart rate from evaluation of a face of the individual in the video and the heart rate may be an equivalent to a blood volume pulse value. The analyzing can use a green channel from the video.

The flow 100 further comprises inferring an individual's mental states based on the heart rate information 140. The mental states can include one or more of frustration, confusion, disappointment, hesitation, cognitive overload, focusing, engagement, attention, boredom, exploration, confidence, trust, delight, disgust, skepticism, doubt, satisfaction, excitement, laughter, calmness, stress, and curiosity. The inferring can include determining arousal 142, determining attention 144, and/or determining valence 146. The method can include interpreting physiological arousal from the heart rate information. Various combinations of the absolute value, relative value, phasic response, and/or tonic response of HR, HRV, BVP, and/or other heart rate information can be used for the inferring. For example, a phasic response of HR can be used to infer attention and a tonic response of HR can be used to infer arousal. A decrease in phasic HR can be used to infer a change of valence with a measure of tonic HR used to infer the direction of the change of valence. In some embodiments, a time lag is factored into the inference 148, as there can be a lag between the video and the stimulus as well as a lag in the individual's heart-rate response to the stimulus. The time-lag factoring can be used to help correlate the response to a specific stimulus. In some embodiments, the flow 100 further comprises aggregating 149 the heart rate information for the individual with other people and/or inferring mental states of the plurality of other people based on the heart rate information on the plurality of other people. Such aggregation can be useful in determining a mental state of the group of people, or a group's response to a certain stimulus.

The flow 100 further comprises analyzing a media presentation based on the mental states which were inferred 150. The media presentation can be any type of media presentation, but can include one or more of an advertisement, a movie, a television show, a web series, a webisode, a video, a video clip, an electronic game, a concept presentation, an e-book, an e-magazine, or an app. Some embodiments further comprise aggregating the mental states for the individual with other people. The analyzing can include comparing the mental state to an intended mental state to determine if the media presentation is effective. So, if the media presentation is an advertisement, the analyzing of the media presentation can include evaluating advertisement effectiveness 152. In some embodiments, different versions of the media presentation are presented and the mental states of the individual or the group can be compared for the different versions. The media presentation can be changed, in some embodiments, based on the mental states. Such changes can include changing a length of the media presentation, adding or deleting scenes, choosing appropriate music for the soundtrack, or other changes. Thus, the analyzing of the media presentation can include optimizing the media presentation 154. The flow 100 can further include learning 160 about heart rate information as part of the analyzing. The learning can factor in one or more previous frames of data and can apply transformations, either previously learned or learned on the fly, to the traces for this analysis to promote the capture of signal fluctuations due to blood flow. One or more previous frames can be used as training data for an individual, for people with similar skin pigmentation, or for people in general. The learning can occur on the fly or can be stored for future use with a certain individual or group of people. The learning can be used for global independent component analysis and/or other transformations. Further, a set of videos can be processed in order to learn heart rate information analysis.

The flow 100 can further comprise collecting facial data based on the video. The facial data can include facial movements, which, in at least some embodiments, can be categorized using the facial action coding system (FACS). The inferring of mental states can be based, at least in part, on the facial data, thus the facial data can be used in combination with the heart rate information for the inferring of mental states. Various steps in the flow 100 may be changed in order, repeated, omitted, or the like without departing from the disclosed concepts. Various embodiments of the flow 100 may be included in a computer program product embodied in a non-transitory computer readable medium that includes code executable by one or more processors.

Figure 2:
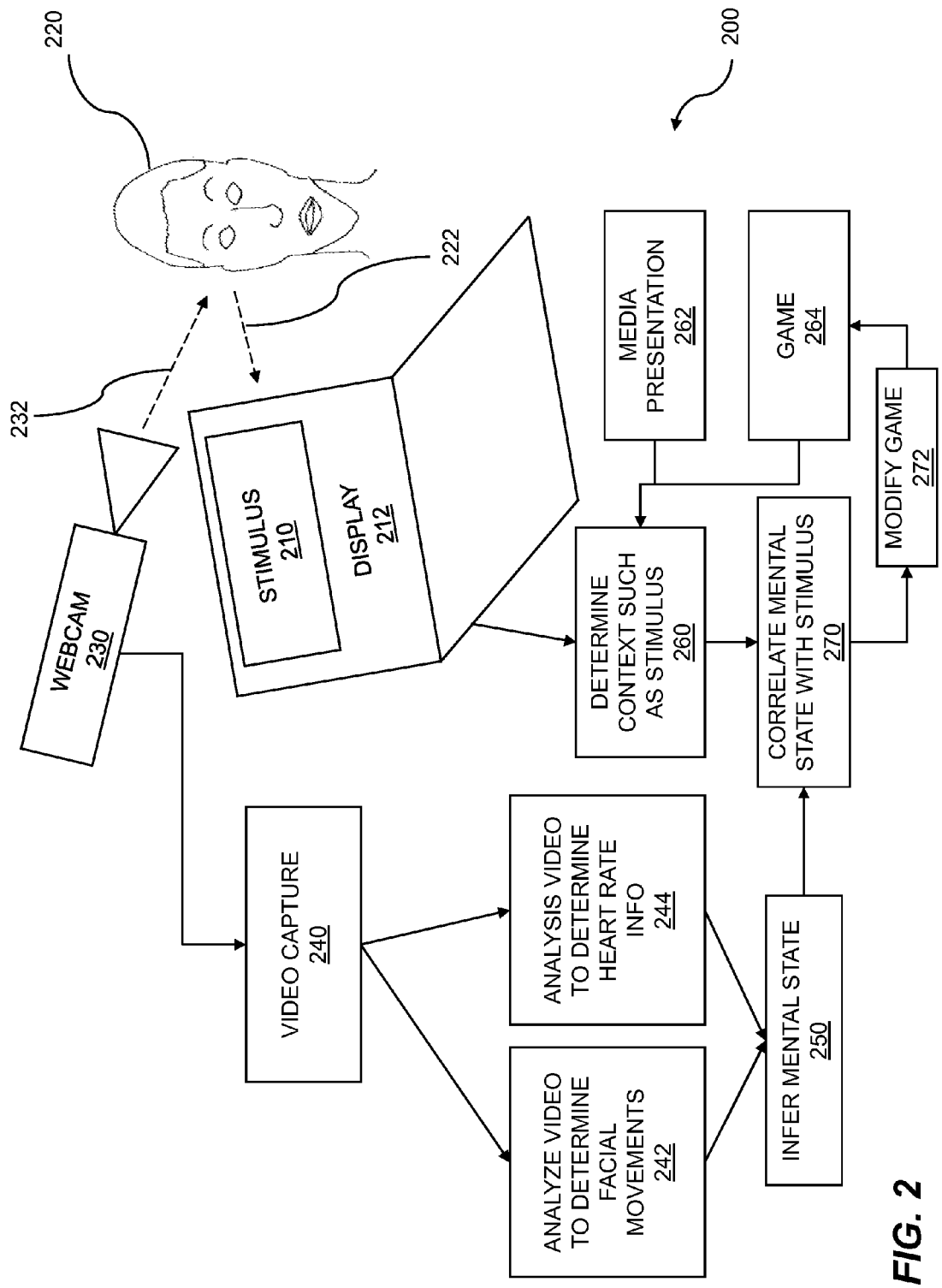
FIG. 2 is a flow diagram for video capture and analysis.

FIG. 2 is a flow diagram 200 for video capture and analysis. An individual 220 can view 222 an electronic display 212 showing a stimulus 210 to the individual 220. The electronic display 212 can be a part of, or can be driven from, a device capturing a video of the individual, or the electronic display can only be loosely coupled or even unrelated to the device capturing the video, depending on the embodiment. The video is captured, in some embodiments, using a mobile device such as a cell phone, a tablet computer, a wearable computing device, or a laptop. The capturing can also be performed with a webcam 230, thus the obtaining the video of the individual comprises capturing the video with a webcam 230, in some embodiments.

The webcam 230 can have a line-of-sight 232 to the user's 220 face, and can capture any one or more of video, audio, and still images of the individual 220. A webcam, as the term is used herein, can include a video camera, a still camera, a thermal imager, a CCD device, a phone camera, a three-dimensional camera, a depth camera, multiple webcams used to show different views of a person, or any other type of image capture apparatus which can allow image data to be captured and used in an electronic system. The images of the person 220 as taken by the webcam 230 can be captured by a video capture unit 240. In some embodiments, video is captured, while in others, one or more still images are captured at regular or irregular intervals. In some embodiments, the one or more still images are used to create a video, which can have a variable frame rate. The captured video or still images can be analyzed to determine one or both of facial movements 242 and heart rate information 244. The facial movements can include information on facial expressions, action units, head gestures, smiles, smirks, brow furrows, squints, lowered eyebrows, raised eyebrows, or attention. In some embodiments, the webcam 230 can also capture images of the setting, which can assist in determining contextual information, other physiological data, gestures, actions, and/or other movements. The analysis of the video can be used to infer a mental state 250 of the user 220.

The flow 200 can further comprise determining contextual information 260, such as identifying the stimulus 210. In some embodiments, the contextual information can include other information such as other individuals nearby who can be captured by the webcam 230, environmental information, identity information about the user 220, or another type of contextual information. The electronic display 212 can include a stimulus 210 such as a media presentation or the user interface of a computer program. Thus, the stimulus 210 can pertain to a media presentation 262. The media presentation 262 can include one of a group consisting of a movie, a television show, a web series, a webisode, a video, a video clip, an electronic game, an e-book, or an e-magazine. In other embodiments, the stimulus 210 can be based on a game 264 device, appliance, vehicle, sensor, application, robot, or system with which the user 220 is interacting using the display 212.

The heart rate information can be correlated 270 to a stimulus that the individual is encountering, and, in at least some embodiments, the inferring factors in the time lag between a stimulus 210 and the heart rate information. This can allow conclusions to be formed about the user's 220 interaction with the stimulus 210. In some embodiments, the media presentation 262 is optimized based on the correlation of the mental state to the stimulus. In some embodiments, a game 264 is changed in some way based on the mental state inferred from the heart rate information and/or the facial movements. Thus, the game 264 can be modified 272 based on the heart rate information. The game can be modified in many different ways. For example, the game's difficulty can be changed, or a player's avatar can be modified to match, modify, or disguise the player's mental state by adjusting the avatar's facial expressions or body actions. That is, in embodiments, the avatar performs an action such as smiling or frowning based on the user's mental state.

Figure 3:
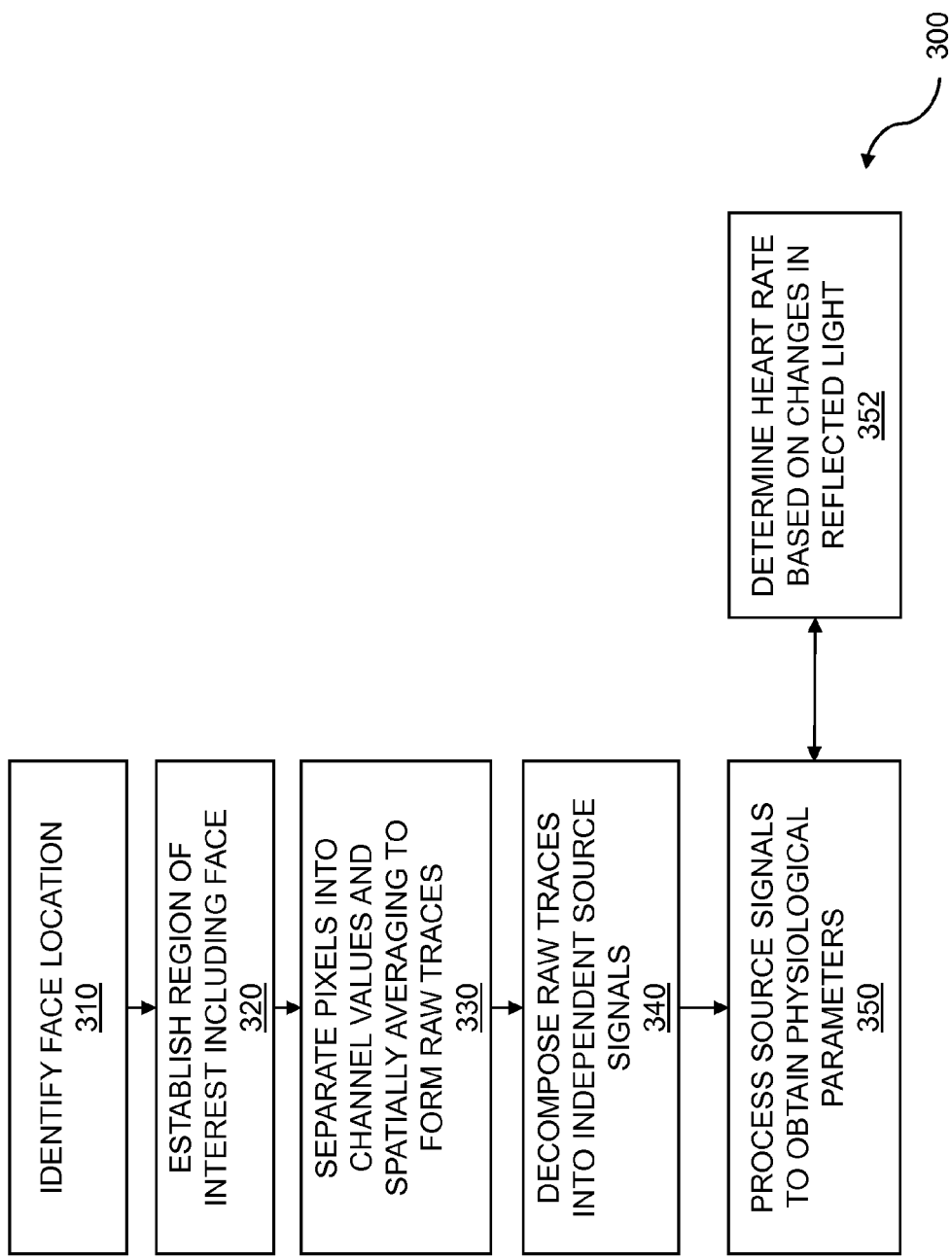
FIG. 3 is flow diagram for determining heart rate information.

FIG. 3 is a flow diagram for determining heart rate information by analyzing video. While the embodiment described in flow 300 has been shown to provide accurate heart rate information from a video, other embodiments can use different algorithms for determining heart rate information by analyzing video. In this embodiment, the analyzing includes identifying a location of a face 310 or a set of faces of an individual or multiple individuals in a portion of a video. Facial detection can be performed using a facial landmark tracker. The tracker can identify points on a face and can be used to localize sub-facial parts such as the forehead and/or cheeks. Further, skin detection can be performed and facial portions removed from images where those portions are considered irrelevant. In some cases eyes, lips, or other portions can be ignored within images. The flow 300 further comprises establishing a region of interest (ROI) including the face 320. In at least one embodiment, the ROI is defined as a portion of a box returned as the location of the face, such as the middle 60% of the width of the box and the full height of the box, for example. In another embodiment the ROI is obtained via skin-tone detection and can be determined using various regions of skin on an individual's body, including non-facial regions. In some embodiments the ROI can be processed using various image processing techniques including, but not limited to, sharpness filters, noise filters, convolutions, and brightness and/or contrast normalization that can operate on a single frame or a group of frames over time. The flow 300 can scale its analysis to process multiple faces within multiple regions of interests (ROI) returned by the facial landmark detector.

The flow 300 can further comprise separating temporal pixel intensity traces in the regions of interest into at least two channel values and spatially and/or temporally processing the separated pixels to form raw traces 330. While one embodiment establishes red, green and blue as channel values, other embodiments can base channels on another color gamut, or other functions of the pixel intensity traces. The channels of the video can be analyzed on a frame-by-frame basis and spatially averaged to provide a single value for each frame in each channel. Some embodiments use a weighted average to emphasize certain areas of the face. One raw trace per channel can be created and can include a single value that varies over time. In some embodiments, the raw traces can be processed for filtering or enhancement. Such processing can include various filters such as low-pass, high-pass, or band-pass filters; interpolation; decimation; or other signal processing techniques. In at least one embodiment, the raw traces are detrended using a procedure based on a smoothness priors approach. Other types of analysis are alternatively possible, such as a feature being extracted from a channel based on a discrete probability distribution of pixel intensities. A histogram of intensities can be generated with a histogram per channel. In some embodiments, one bin can be considered equivalent to summing spatially. Analysis can include tracing fluctuations in reflected light from the skin of a person being viewed.

The flow 300 can further comprise decomposing the raw traces into at least one independent source signal 340. The decomposition can be accomplished using independent component analysis (ICA). Independent component analysis (ICA) is a technique for uncovering independent signals from a set of observations composed of linear mixtures of underlying sources. In this case, the underlying source signal of interest can be BVP. During the cardiac cycle, volumetric changes in the blood vessels modify the path length of the incident ambient light, which in turn changes the amount of light reflected, a measurement which can indicate the timing of cardiovascular events. By capturing a sequence of images of the facial region with a webcam, the red, green and blue (RGB) color sensors pick up a mixture of reflected plethysmographic signals along with other sources of fluctuations in light due to artifacts. Given that hemoglobin absorptivity differs across the visible and near-infrared spectral range, each color sensor records a mixture of the original source signals with slightly different weights. The ICA model assumes that the observed signals are linear mixtures of the sources where one of the sources is hemoglobin absorptivity or reflectivity. ICA can be used to decompose the raw traces into a source signal representing hemoglobin absorptivity correlating to BVP. Respiration rate information is also determined, in some embodiments.

The flow 300 further comprises processing at least one source signal to obtain the heart rate information 350. Heart rate (HR) can be determined by observing the intervals between peaks of the source signal, finding the peaks having been discussed above. Thus, the heart rate information can include heart rate, and the heart rate can be determined based on changes in the amount of reflected light 352. Heart rate variability, both phasic and tonic, can be obtained using a power spectral density (PSD) estimation and/or through other signal processing techniques. The analysis can include evaluation of phasic and tonic heart rate responses. In some embodiments, the video includes a plurality of other people. Such embodiments can comprise identifying locations for faces of the plurality of other people and analyzing the video to determine heart rate information on the plurality of other people. Various steps in the flow 300 may be changed in order, repeated, omitted, or the like without departing from the disclosed concepts. Various embodiments of the flow 300 may be included in a computer program product embodied in a non-transitory computer readable medium that includes code executable by one or more processors. In other embodiments, a supervised learning approach is adopted to the problem of detecting human heart rate. A statistical classifier can be trained by learning from a data set consisting of human blood volume pulse synchronized with face videos. The classifier will recognize a pulse by learning patterns of variability, in the mean of the green channel, that correspond to a beat in the blood volume pulse values. After training, the classifier can process a sequence of frames and thereby report a heartbeat when it detects a pattern in the green channel similar to the pattern seen during training. The classifier can return a number that could be positive or negative. A larger number is returned as a result of a higher confidence by the classifier. In some embodiments, progressive filtering can be used to enable shorter time spans in the heart rate analysis. In some cases each beat can be evaluated for a heart rate. In embodiments, facial images can be compensated for media images that are reflected from the face due to screen lighting.

Figure 4:
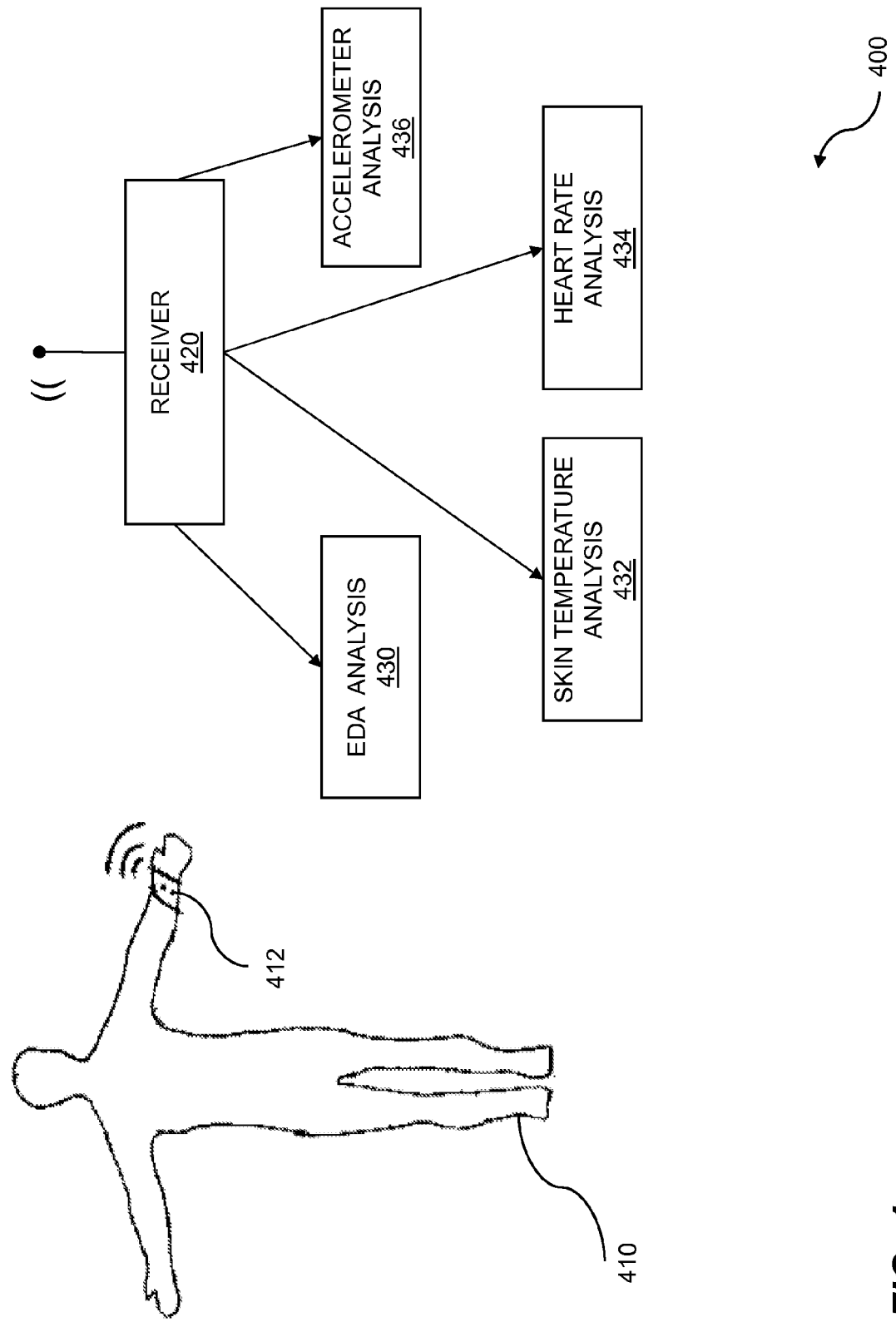
FIG. 4 is a diagram showing sensor analysis.

FIG. 4 is a diagram showing sensor analysis. The diagram 400 comprises obtaining biosensor data for the individual 410. Data can be collected from a person 410 as he or she interacts with a computer or views a media presentation. The person 410 can have a biosensor 412 attached to him or her for the purpose of collecting mental state data. The biosensor 412 can be placed on the wrist, palm, hand, head, or another part of the body. In some embodiments, multiple biosensors are placed on the body in multiple locations. The biosensor 412 can include detectors for physiological data such as electrodermal activity, skin temperature, accelerometer readings, and the like. Other detectors for physiological data can also be included, such as heart rate, blood pressure, EKG, EEG, other types of brain waves, and other physiological detectors. The biosensor 412 can transmit collected information to a receiver 420 using wireless technology such as Wi-Fi, Bluetooth, 802.11, cellular, or other protocols. In other embodiments, the biosensor 412 communicates with the receiver 420 using other methods such as a wired or optical interface. The receiver can provide the data to one or more components in the system 400. In some embodiments, the biosensor 412 records multiple types of physiological information in memory for later download and analysis. In some embodiments, the download of recorded physiological data is accomplished through a USB port or another form of wired or wireless connection. The biosensor data can augment the heart rate information determined by analyzing video of the person 410.

Mental states can be inferred based on physiological data, including physiological data from the sensor 412 which can be used to augment the heart rate information determined by analyzing video. Mental states can also be inferred, at least in part, based on facial expressions and head gestures observed by a webcam, or based on a combination of data from the webcam and data from the sensor 412. The mental states can be analyzed based on arousal and valence. Arousal can range from being highly activated, such as when someone is agitated, to being entirely passive, such as when someone is bored. Valence can range from being very positive, such as when someone is happy, to being very negative, such as when someone is angry. Physiological data can include one or more of electrodermal activity (EDA), heart rate, heart rate variability, skin temperature, respiration, accelerometer readings, and other types of analysis of a human being. It will be understood that both here and elsewhere in this document, physiological information can be obtained either by biosensor 412 or by facial observation via an image capturing device. Facial data can include facial actions and head gestures used to infer mental states. Further, the data can include information on hand gestures or body language and body movements such as visible fidgets. In some embodiments, these movements are captured by cameras, while in other embodiments these movements are captured by sensors. Facial data can include the tilting of the head to the side, leaning forward, smiling, and frowning, among numerous other gestures or expressions.

In some embodiments, electrodermal activity is collected continuously, periodically, or sporadically. The electrodermal activity can be analyzed 430 to indicate arousal, excitement, boredom, or other mental states based on observed changes in skin conductance. Skin temperature can be collected and recorded. In turn, the skin temperature can be analyzed 432. Changes in skin temperature can indicate arousal, excitement, boredom, or other mental states. Heart rate can be collected and recorded, and can also be analyzed 434. A high heart rate can indicate excitement, arousal, or other mental states. Accelerometer data can be collected and used to track one, two, or three dimensions of motion. The accelerometer data can be recorded. The accelerometer data can be analyzed 436 and can indicate a sleep pattern, a state of high activity, a state of lethargy, or other states. The various data collected by the biosensor 412 can be used along with the heart rate information determined by analyzing video captured by the webcam in the analysis of mental state.

Figure 5:
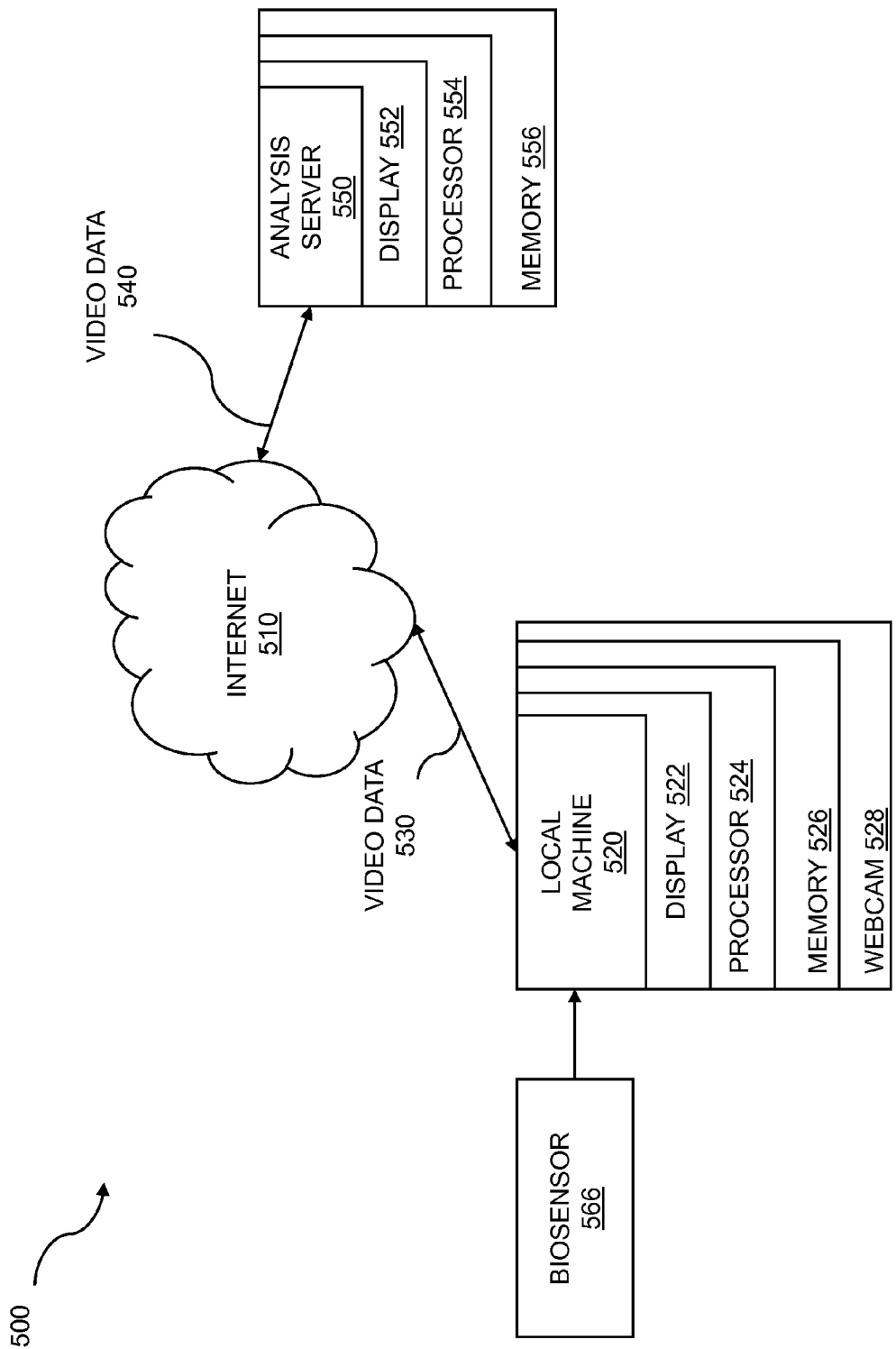
FIG. 5 is a system diagram for mental state analysis.

FIG. 5 is a system diagram 500 for mental state analysis. The system 500 can include a local machine 520 with which an individual is interacting. The local machine 520 can include one or more processors 524 coupled with a memory 526 that can be used to store instructions and data. In some embodiments, the local machine 520 is a mobile device, including, but not limited to, a laptop, a personal computer, a tablet computer, a cell phone, a smart phone, a vehicle mounted computer, a wearable computer, and so on. The local machine 520 can also include a display 522 which can be used to show a stimulus to the individual, such as a media presentation, a game, or a computer program user interface. The display 522 can be any electronic display, including but not limited to, a computer display, a laptop screen, a net-book screen, a tablet screen, a cell phone display, a mobile device display, an automotive type display, a remote with a display, a television, a projector, or the like. The local machine can also include a webcam 528 capable of capturing video and still images of the user interacting with the local machine 520. The webcam 528, as the term is used herein, can refer to a camera on a computer (such as a laptop, a net-book, a tablet, a wearable device, or the like), a video camera, a still camera, a cell phone camera, a camera mounted in a transportation vehicle, a wearable device including a camera, a mobile device camera (including, but not limited to, a forward facing camera), a thermal imager, a CCD device, a three-dimensional camera, a depth camera, multiple webcams used to capture different views of viewers, or any other type of image capture apparatus that allows image data to be captured and used by an electronic system. In some embodiments, one or more biosensors 566 can be coupled to the local machine 520. The biosensor or biosensors 566 can monitor the individual interacting with the local machine 520 to obtain physiological information on the individual.

The one or more processors 524 can be configured to obtain video of the individual using the webcam or other camera; analyze the video to determine heart rate information; and infer mental states of the individual based, at least in part and in some embodiments, on the heart rate information. So, the system can comprise a computer program product embodied in a non-transitory computer readable medium for mental state analysis, the computer program product comprising code for obtaining video of an individual, code for analyzing the video to determine heart rate information, and code for inferring mental states of the individual based on the heart rate information.

Some embodiments include an analysis server 550, although some embodiments comprise performing the analysis of the video data, inferring mental states, and executing other aspects of methods described herein on the local machine 520. The local machine 520 sends video data 530 over the Internet 510 or other computer communication link to the analysis server 550, in some embodiments. In some embodiments, the analysis server 550 is provisioned as a web service. The analysis server 550 includes one or more processors 554 coupled to a memory 556 to store instructions and/or data. Some embodiments of the analysis server 550 include a display 552. The one or more processors 554 can be configured to receive video data 540 from the local machine 520 over the Internet 510. Thus, the obtaining the video of the individual can comprise receiving the video from another computer, and the obtaining the video of the individual can comprise receiving the video over the Internet. The transfer of video can be accomplished once an entire video is captured of a person for analysis. Alternatively, video can be streamed as it is collected. The video can be analyzed for heart rate information on the fly as the video is collected or as it is streamed to analysis machine. The one or more processors 554 can also be configured to analyze the video 540 to determine heart rate information, and infer mental states of the individual based on the heart rate information. In some embodiments, the analysis server receives video of multiple individuals from multiple other computers, and determine heart rate information for the multiple individuals. In some embodiments, the heart rate information from the multiple individuals is aggregated to determine an aggregated mental state of the group including the multiple individuals.

Each of the above methods may be executed on one or more processors on one or more computer systems. Embodiments may include various forms of distributed computing, client/server computing, and cloud based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for mental state analysis comprising:
    obtaining video of an individual;
    analyzing the video to determine heart rate information, wherein the analyzing includes:
        evaluation of phasic and tonic heart rate responses;
        identifying a location of a face of the individual in a portion of the video;
        separating pixels, from the location of the face, from the video of the individual, into at least a green pixel temporal intensity trace;
        training a statistical classifier, wherein the training is learned from a data set consisting of human blood volume pulse synchronized face videos; and
        recognizing a pulse, from the video of the individual, using the statistical classifier, by learning patterns of variability in the mean of the pixel temporal intensity trace;
    correlating the heart rate information to a stimulus that the individual is encountering; and
    inferring, using one or more processors, mental states of the individual based on the heart rate information, wherein a time lag between the stimulus and the heart rate information is factored into the inferring.

2. The method of claim 1 further comprising analyzing a media presentation based on the mental states, which were inferred.

3. The method of claim 2 wherein the analyzing the media presentation includes evaluating advertisement effectiveness.

4. The method of claim 2 wherein the analyzing the media presentation includes optimizing the media presentation.

5. The method of claim 2 wherein the analyzing a media presentation is further based on learning about heart rate information.

6. The method of claim 5 wherein the learning further comprises factoring in one or more previous frames of data of the obtained video.

7. The method of claim 6 wherein the learning includes learned on-the-fly transformations.

8. The method of claim 6 further comprising promoting the capture of heart rate signal fluctuations in the analyzed video due to blood flow.

9. The method of claim 1 wherein the stimulus pertains to a media presentation or is based on a game.

10. The method of claim 9 wherein the game is modified based on the heart rate information.

11. The method of claim 1 further comprising aggregating the heart rate information for the individual with other people.

12. The method of claim 1 further comprising aggregating the mental states for the individual with other people.

13. The method of claim 1 wherein learning about heart rate information is included as part of the analyzing.

14. The method of claim 1 wherein the inferring includes determining arousal, attention, or valence.

15. The method of claim 1 wherein the analyzing includes calculating blood volume pulse.

16. The method of claim 1 wherein the analyzing factors in an occlusion of part of a face for the individual.

17. The method of claim 1 further comprising determining contextual information.

18. The method of claim 1 further comprising establishing a region of interest including the face, separating pixels in the region of interest into at least two channel values and combining to form raw traces, transforming and decomposing the raw traces into at least one independent source signal, and processing the at least one independent source signal to obtain the heart rate information.

19. The method of claim 18 wherein the heart rate information includes heart rate and the heart rate is determined based on changes in an amount of reflected light.

20. The method of claim 1 wherein the video includes a plurality of other people.

21. The method of claim 20 further comprising identifying locations for faces of the plurality of other people and analyzing the video to determine heart rate information on the plurality of other people.

22. The method of claim 21 further comprising inferring mental states of the plurality of other people based on the heart rate information on the plurality of other people.

23. The method of claim 1 further comprising obtaining biosensor data for the individual.

24. The method of claim 23 wherein the biosensor data augments the heart rate information.

25. The method of claim 23 wherein the biosensor data includes one or more of electrodermal activity, heart rate, heart rate variability, skin temperature, or respiration.

26. The method of claim 1 further comprising collecting facial data based on the video.

27. The method of claim 26 wherein the facial data includes facial movements.

28. The method of claim 27 wherein the inferring is based on the facial data.

29. The method of claim 27 wherein the facial data is used in combination with the heart rate information.

30. The method of claim 1 wherein the mental states include one or more of frustration, confusion, disappointment, hesitation, cognitive overload, focusing, engagement, attention, boredom, exploration, confidence, trust, delight, disgust, skepticism, doubt, satisfaction, excitement, laughter, calmness, stress, sentimentality, and curiosity.

31. A computer program product embodied in a non-transitory computer readable medium for mental state analysis, the computer program product comprising code which causes one or more processors to perform operations of:
obtaining video of an individual;
analyzing the video to determine heart rate information, wherein the analyzing includes:
evaluation of phasic and tonic heart rate responses;
identifying a location of a face of the individual in a portion of the video;
separating pixels, from the location of the face, from the video of the individual, into at least a green pixel temporal intensity trace;
training a statistical classifier, wherein the training is learned from a data set consisting of human blood volume pulse synchronized face videos; and
recognizing a pulse, from the video of the individual, using the statistical classifier, by learning patterns of variability in the mean of the pixel temporal intensity trace;
correlating the heart rate information to a stimulus that the individual is encountering; and
inferring mental states of the individual based on the heart rate information, wherein a time lag between the stimulus and the heart rate information is factored into the inferring.

32. A computer system for mental state analysis comprising:
a memory which stores instructions;
one or more processors attached to the memory wherein the one or more processors, when executing the instructions which are stored, are configured to:
obtain video of an individual;
analyze the video to determine heart rate information, wherein analyzing includes:
evaluation of phasic and tonic heart rate responses;
identifying a location of a face of the individual in a portion of the video;
separating pixels, from the location of the face, from the video of the individual, into at least a green pixel temporal intensity trace;
training a statistical classifier, wherein the training is learned from a data set consisting of human blood volume pulse synchronized face videos; and
recognizing a pulse, from the video of the individual, using the statistical classifier, by learning patterns of variability in the mean of the pixel temporal intensity trace;
correlate the heart rate information to a stimulus that the individual is encountering; and
infer mental states of the individual based on the heart rate information, wherein a time lag between the stimulus and the heart rate information is factored into an inference.

* * * * *